(12) United States Patent
Ashraf et al.

(10) Patent No.: US 8,357,638 B2
(45) Date of Patent: Jan. 22, 2013

(54) OLIGONUCLEOTIDE LIBRARY ENCODING RANDOMISED PEPTIDES

(75) Inventors: Mohammed Ashraf, Birmingham (GB); Marcus Daniel Hughes, Manchester (GB); Anna Victoria Hine, Kidderminster (GB)

(73) Assignee: Aston University, Birmingham (GB)

( * ) Notice: Subject to any disclaimer, the term of this patent is extended or adjusted under 35 U.S.C. 154(b) by 974 days.

(21) Appl. No.: 11/989,087

(22) PCT Filed: Jul. 18, 2006

(86) PCT No.: PCT/GB2006/002672
§ 371 (c)(1),
(2), (4) Date: Feb. 13, 2009

(87) PCT Pub. No.: WO2007/010243
PCT Pub. Date: Jan. 25, 2007

(65) Prior Publication Data
US 2009/0264313 A1    Oct. 22, 2009

(30) Foreign Application Priority Data
Jul. 22, 2005  (GB) ................................ 0515131.1

(51) Int. Cl.
*C40B 50/06* (2006.01)
(52) U.S. Cl. ................ 506/26; 506/17; 506/18
(58) Field of Classification Search ........................ None
See application file for complete search history.

(56) References Cited

U.S. PATENT DOCUMENTS

| 5,702,892 A * | 12/1997 | Mulligan-Kehoe ............. 506/14 |
| 5,869,295 A | 2/1999 | LaBean et al. |
| 2009/0053761 A1 * | 2/2009 | Jones ........................... 435/69.1 |

FOREIGN PATENT DOCUMENTS

| WO | 00/15777 | 3/2000 |
| WO | 00/63360 | 10/2000 |
| WO | 03/106679 | 12/2003 |

OTHER PUBLICATIONS

Pinilla, C., et al., "Advances in the Use of Synthetic Combinatorial Chemistry: Mixture-Based Libraries," *Nature Medicine*, Jan. 2003, vol. 9, pp. 118-122.
Hughes, M.D., et al., "Removing the Redundancy from Randomised Gene Libraries,"*J. Mol. Biol.*, 2003, vol. 331, pp. 973-979.
Larsson, O., et al., "Quantitative Codon Optimisation of DNA Libraries Encoding Sub-Random Peptides: Design and Characterisation of a Novel Library Encoding Transmembrane Domain Peptides," *Nucleic Acids Research*, 2002 Oxford University Press, vol. 30, No. 23.

* cited by examiner

*Primary Examiner* — Christopher M Gross
(74) *Attorney, Agent, or Firm* — Todd E. Garabedian; Wiggin and Dana LLP

(57) ABSTRACT

The invention relates to a method of producing an oligonucleotide library comprising a plurality of oligonucleotides, each oligonucleotide in the library having at least one predetermined position, a randomization codon selected from a defined group of codons, the codons within the defined group coding for different amino acids. Vector, host cells containing such libraries and kits for the production of such libraries are also provided.

16 Claims, 3 Drawing Sheets

OLIGONUCLEOTIDE LIBRARY ENCODING RANDOMISED PEPTIDES

CROSS-REFERENCE TO RELATED APPLICATIONS

This application is a U.S. National Stage application of International Application Ser. No. PCT/GB2006/002672 filed Jul. 18, 2006.

The present application claims foreign priority to application 0515131.1 filed Jul. 22, 2005 in the United Kingdom.

The invention relates to the production of oligonucleotide libraries encoding randomised peptides, vectors and host cells containing such libraries, and kits for the production of such libraries.

Combinatorial techniques for the production of peptides have been available since the 1960's and have included solid-phase synthesis of peptides and additionally the parallel solid-phase synthesis methods developed in the 1980's. Such techniques are reviewed in the article by Pinilla C., et al. (*Nature Medicine* (2003), Vol. 9, pages 118-122).

The production of DNA libraries coding for different peptides is itself well-known in the art. Randomised gene libraries have little in common with conventional genomic or cDNA libraries. Conventional libraries consist of clones that collectively cover an entire genome/transcriptome and are generally screened by nucleic acid hybridisation. In contrast, randomised libraries generally contain variations of a gene or a fragment of a gene, which is screened for novel activity. The randomised genes are expressed and screened conventionally, for example, in phage, bacterial or in vitro display techniques.

Conventionally, standard gene randomisation techniques obligate the cloning of an excess of genes using either NNN or $NN^G/T$ codons, where N=A, C, G and T, 64 or 32 codons must be cloned, respectively, to ensure representation of all 20 amino acids. At first, these numbers may appear relatively small but if we consider multiple positions of randomisation there is an exponential relationship between the number of genes cloned and the number of proteins obtained. Hine et al have previously described an alternative method for producing DNA libraries, 'MAX' randomisation, in which two or more positions are randomised such that all 20 amino acids, or a subset thereof, are represented (PCT publication WO 00/15777). This methodology requires a pool of oligonucleotides, for each position to be randomised, which are hybridised to a template, conventionally (NNN) randomised at the appropriate positions. This approach enables each amino acid to be encoded only once within the pools of oligonucleotides, hence the number of unique genes generated is equivalent to the number of proteins encoded, regardless of the number of positions of randomisation. Although this methodology represents a significant improvement over traditional techniques, there remains a relatively high percentage of non-MAX (unwanted) codons (~10%) at the randomised positions. Additionally, due to the constraints of the hybridisation process only small quantities of the DNA constructs are produced, which is difficult to manipulate particularly when encoding subsets of amino acids.

Subsequently Hine et al have made improvements to this methodology which virtually eliminate the presence of unwanted sequences and increase the yield of DNA (Hine, A. V., Hughes, M. D., Nagel, D. A., Ashraf, M. and Santos, A. F. (2002). MAX Codon Gene Libraries. WO 03/106679; Hughes M. D., Nagel D. A., Santos A. F., Sutherland A. J. and Hine A. V. (2003). Removing the redundancy from randomised gene libraries. *J. Mol. Biol.* 331 (5), 973-979). This methodology employs some additional oligonucleotides which hybridise to the template strand but also provide an extension which is not complementary to the template strand. This enables the selective amplification of the required encoding strand thus increasing the yield and minimising unwanted sequences.

The problem associated with prior art methods has been the production of more than two contiguous randomised codons. This is important to allow stretches of several amino acids in a sequence to be randomised. Variations of the methods described in, for example, WO 03/106679 only allow two continuous codons to be randomised as they require the use of flanking oligonucleotide sequences to hybridise to the template strands. Furthermore, such methods require the production of a randomised template strand to be produced, prior to using selection oligonucleotides. Potentially this limits the number of codons that can be randomised because of the complexity/mass of the template oligonucleotide.

The inventors tried a number of techniques in which to randomise three or more consecutive oligonucleotides which proved to be difficult to carry out or alternatively produce some satisfactory results. These included trying to ligate three or more MAX trinucleotides randomly into a single-strand oligonucleotide using RNA ligase. This latter technique proved to work very poorly and subsequently PCR amplification led to smears in which individual species could not be isolated by the inventors. The addition of MAX codons, containing 3 nucleotides, ligated directly onto the blunt end of an oligonucleotide also proved to be difficult.

The technique now identified and described by the inventors unexpectedly allows the production of contiguous randomised codons without the need to produce randomised template oligonucleotides.

The invention provides a method of producing an oligonucleotide library comprising a plurality of oligonucleotides, each oligonucleotide in the library having at least one predetermined position, a randomisation codon selected from a defined group of codons, the codons within said defined group coding for different amino acids, said method comprising the steps of:
(a) Providing one or more double-stranded starter oligonucleotides;
(b) Providing a plurality of different double stranded randomisation oligonucleotides comprising:
    (i) a coding strand, the coding strand comprising a randomisation codon; and
    (ii) a substantially complementary non-coding strand,
wherein each double-stranded randomisation oligonucleotide comprises a nucleotide sequence coding for a restriction endonuclease recognition site capable of being recognised by a restriction endonuclease, the restriction endonuclease capable of cleaving the randomisation oligonucleotide upstream or downstream of the endonuclease recognition site at a predetermined cleavage site to create a blunt ended cut;
(c) Ligating each double-stranded starter oligonucleotide to a double-stranded randomisation oligonucleotide to form ligated oligonucleotides;
(d) Amplifying the ligated oligonucleotides;
(e) Digesting the ligated oligonucleotide with the restriction endonuclease to form a plurality of randomised double-stranded oligonucleotides, each of which comprise, at one end, a randomisation codon (and its complementary sequence); and, optionally,
(f) Using the randomised double-stranded oligonucleotides as starter oligonucleotides and repeating method steps (a) to (e) and optionally step (f) to produce a plurality of randomised double-stranded oligonucleotides, each comprising an additional randomisation codon.

The randomisation oligonucleotides differ by having different randomisation codons.

The oligonucleotides used are preferably DNA, however other double-stranded nucleotides, such as RNA, or analogues of DNA or RNA may be used.

Preferably, the double-stranded starter oligonucleotides comprise a blunt end onto which the double-stranded randomisation oligonucleotides are ligated.

The randomisation codon on the coding strand and the complementary codon on the non-coding strand preferably form a blunt end on the randomisation oligonucleotides and are preferably ligated to the blunt end of the double-stranded starter oligonucleotide.

At least a portion of the starter oligonucleotide to which the randomisation codon attaches may encode a part of a gene or other nucleotide sequence encoding a predetermined amino acid sequence.

Preferably, the randomisation oligonucleotides and the starter oligonucleotides are ligated by DNA ligase. DNA ligases are well-known in the art. For example, *E. coli* and phage T4 encode an enzyme, DNA ligase, which seals single-stranded nicks between adjacent oligonucleotides in a duplex DNA chain. The requirement of the different enzymes are well-known. For example, T4 enzyme requires ATP whilst the *E. coli* enzyme requires $NAD^+$. In each case, the cofactor is split and forms an enzyme-AMP complex. The complex binds either side of the DNA strands to be joined and makes a covalent bond between a 5'-phosphate on one strand and a 3'-OH group on the adjacent strand.

Hence, preferably at least one of the 5' ends of the oligonucleotides to be ligated comprises a phosphate group to allow the oligonucleotides to be ligated by a DNA ligase.

Preferably, both of the 5' ends of the oligonucleotides to be ligated comprise a phosphate group. Preferably the adjacent strand to the phosphate group(s) will contain a 3'-OH group.

Preferably, the predetermined cleavage site for the endonuclease is immediately adjacent to the randomisation codon.

The ligated oligonucleotides may be amplified by, for example, PCR using primers complementary to e.g. sequences on the starter oligonucleotides.

The PCR product produced may be purified and isolated, for example, using conventional techniques such as polyacrylamide gel electrophoresis (PAGE) and excision of the relevant band of DNA prior to isolation of the DNA and digestion with the restriction endonuclease.

Preferably step (f) is followed one or more times to be used to an oligonucleotide library comprising a plurality of oligonucleotides, each oligonucleotide and library having at least two contiguous randomised codons. Most preferably, the number of randomised codons contained in the library is 1 or 2, most preferably 3, 4, 5, 6, 7, 8, 9 or 10 codons.

Preferably the method provides ligating a double stranded completion oligonucleotide to the starter oligonucleotide after the required number of randomised codons have been added. The completion oligonucleotide may comprise a predefined nucleotide sequence comprising a restriction endonuclease recognition site to allow the randomised nucleotide sequence to be spliced into a gene of interest. Alternatively, for example, the completion oligonucleotide may encode a non-randomised fragment of a gene of interest.

A nucleotide sequence attached to the randomisation codon of the randomisation oligonucleotide may be different in each round of adding the randomisation codons. That is each set of randomisation oligonucleotides used in each round of steps (a) to (f), when the method is repeated to add further randomised codons, may contain a different sequence attached to the randomised codon. This allows randomised double-stranded oligonucleotides obtained after each round of random codon addition to be selectively amplified by PCR with a primer complementary to the different sequence. This is expected to reduce the need for PAGE purification between random codon addition cycles.

Preferably, the restriction endonuclease recognition site and cleavage site is:

```
5'-GAGTCNNNNN^-3'      (SEQ. ID. No. 1)

3'-CTCAGNNNNN^-5'      (SEQ. ID. No. 2)
``` where—N=any nucleotide
^=the restriction endonuclease cleavage site.

Such a restriction endonuclease site has been identified as being recognised by two restriction endonucleases: MlyI, which is obtainable from New England Biolabs, Inc. and SchI, available from Fermentas Life Sciences. The two enzymes are produced by different micro-organisms. MlyI, for example, is described in U.S. Pat. No. 6,395,531 and is found in *Micrococcus lylae*. Both of the endonucleases recognise the double-stranded DNA sequence 5'-GAGTC 3' and cleave DNA 5 bases downstream generating blunt ends. However, any restriction endonuclease which binds to a restriction endonuclease sequence but cuts adjacent to or a number of nucleotides upstream or downstream of the recognition sequence to allow separation of the randomisation codon may also be used.

The genetic coding for different amino acids is well-known, for example the genetic code for codons in mRNA transcribed from the codon DNA strand is:

|   | U | | C | | A | | G | | |
|---|---|---|---|---|---|---|---|---|---|
| U | UUU<br>UUC | Phe | UCU<br>UCC<br>UCA<br>UCG | Ser | UAU<br>UAC | Tyr | UGU<br>UGC | Cys | U<br>C |
|   | UUA<br>UUG | Leu |   |   | UAA*<br>UAG* | Stop<br>Stop | UGA*<br>UGG | Stop<br>Trp | A<br>G |
| C | CUU<br>CUC<br>CUA<br>CUG | Leu | CCU<br>CCC<br>CCA<br>CCG | Pro | CAU<br>CAC | His | CGU<br>CGC<br>CGA<br>CGG | Arg | U<br>C<br>A<br>G |
|   |   |   |   |   | CAA<br>CAG | Gln |   |   |   |
| A | AUU<br>AUC<br>AUA | Ile | ACU<br>ACC<br>ACA<br>ACG | Thr | AAU<br>AAC | Asn | AGU<br>AGC | Ser | U<br>C |
|   | AUG** | Met |   |   | AAA<br>AAG | Lys | AGA<br>AGG | Arg | A<br>G |
| G | GUU<br>GUC<br>GUA | Val | GCU<br>GCC<br>GCA<br>GCG | Ala | GAU<br>GAC | Asp | GGU<br>GGC<br>GGA<br>GGG | Gly | U<br>C<br>A<br>G |
|   | GUG** |   |   |   | GAA<br>GAG | Glu |   |   |   |

*Chain-terminating, or "nonsense" codons.

**Also used to specify the initiator formyl-Met-tRNAMet. The Val triplet GUG is therefore "ambiguous" in that it codes both valine and methionine.

The different amino acids coded by different codons have different properties. In some circumstances it may be desirable to focus the library towards different groups of amino acids with similar properties. Hence, preferably the codons are selected. For example, they may be focused towards very hydrophobic amino acids (such as Val, Ile, Leu, Met, Phe, Trp or Cys.), less hydrophobic amino acids (Ala, Tyr, His, Thr, Ser, Pro and Gly), part-hydrophobic amino acids (Arg and Lys), sulphur-containing amino acids (Cys), positively charged amino acids (Arg, His and Lys), negatively-charged amino acids (Asp and Glu), etc. Alternatively, they may be selected to avoid a particular amino acid, such as Pro or Cys.

Preferably at least 2, 3, 4, 5, 6, 7, 8, 9, 10, 11, 12, 13, 14, 15, 16, 17, 18, 19 or 20 different randomisation codons are used in each round of randomisation codon addition.

Not all codons are efficiently used in any particular organism. Hence, preferably the codons are specifically selected to allow the randomised DNA library to be efficiently utilised in any host cell used for expressing the DNA library and producing peptides from it. The problems associated with not utilising randomised libraries efficiently are summarised in the article by Hughes M. D., et al. (*J. Mol. Biol.* (2003), Vol. 331, pages 973-979).

Preferably, the codons are selected for favoured codons for the expression of each amino acid in a selected organism. For example, for *E. coli*, the codons are preferably GCG (A), TGC (C), GAT (D), GAA (E), TTT (F), GGC (G), CAT (H), ATT (I), AAA (K), CTG (L), ATG (M), AAC(N), CCG (P), CAG (O), CGC(R), AGC (S), ACC (T), GTG (V), TGG (W) and TAT (Y). The letters in brackets indicate the amino acid coded by the codon.

Preferably, the 3' end of the coding strand comprises a blocking group to prevent nonproductive ligation of, for example, multiple copies of the randomisation oligonucleotides. The blocking group may be selected from an amino acid, a phosphate group, a glyceryl moiety, a thiol group or, for example, a polyethylene glycol moiety.

Additionally, or alternatively, the non-coding strand may comprise, at it's 5' end, one or more nucleotides extending beyond the 3' end of the complementary coding strand. This again reduces the number of nonproductive ligations occurring.

Preferably, the methods of the invention additionally comprise the steps of:

(g) Providing a randomised double-stranded starter oligonucleotide produced by a method according to any preceding claim;

(h) Providing a predefined oligonucleotide comprising:
   (i) a coding strand, the coding strand comprising a predefined codon coding for a predefined amino acid; and
   (ii) a substantially complementary non-coding strand,
wherein the predefined oligonucleotide comprises a nucleotide sequence coding for a restriction endonuclease recognition site capable of being recognised by a restriction endonuclease, the restriction endonuclease capable of cleaving the predefined oligonucleotide upstream or downstream of the endonuclease recognition at a predetermined cleavage site to create a blunt ended cut;

(i) Ligating the randomised double-stranded starter oligonucleotide to the predefined oligonucleotide to form a ligated oligonucleotide;

(j) Amplify the ligated oligonucleotide; and (k) Digest the ligated oligonucleotide with the restriction endonuclease to form a randomised oligonucleotide comprising at one end the predefined codon.

The predefined codon is preferably at one end of the predefined oligonucleotide.

This allows the insertion of a known amino acid into a predetermined position of the peptide produced by the oligonucleotide libraries. The advantage of this technique is that it allows the effect of any particular amino acid in that predefined library to be studied. Examples of such positional scanning libraries are discussed in, for example, the article by Pinilla (*Nature Medicine* (2003), Vol. 9, pages 118-122). The method of the invention allows the production of such positional scanning libraries to be achieved relatively rapidly and relatively easily.

One or more additional random codons may be added to an end of the predefined codon using the methods of the invention. The restriction endonuclease recognition site, restriction endonuclease, blocking group and/or optional extension groups to the 3' end of the non-coding strand may be as defined above.

The randomised oligonucleotide comprising the predefined codon may then be used as a starter oligonucleotide to add one or more additional random codons.

Preferably, the coding strand of the randomisation oligonucleotide used in the method of the invention comprises the sequence:

(i)     5' XXX^(N)$_a$R'(N)$_b$-B 3'
or (ii)    5'-(N)$_b$R(N)$_a$^XXX-3' where:
XXX is the randomisation codon,
N is any nucleotide,
a is an integer of 0 to 10, preferably 5,
b is an integer of 0 to 40, preferably 1 to 20, or preferably 1 to 10,
^ is the restriction endonuclease cleavage site,
R' is the reverse complement of the restriction endonuclease recognition site sequence,
R is the restriction endonuclease recognition site sequence,
B may or may not be present and may be selected from —OH, —NH$_2$,
phosphate, a glyceryl moiety, a thiol and a polyethylene glycol moiety.

The second randomised oligonucleotide (ii) may be used to ligate to the 5' end of the starter oligonucleotide.

Preferably, the oligonucleotides obtained by the methods of the invention are inserted into a suitable expression vector. Expression vectors, for example for expressing the peptides encoded by the oligonucleotides, are well-known in the art. For example, phage expression libraries in which oligonucleotides are inserted into the nucleotide sequence coding for phage coat proteins, so that the peptides encoded by them are expressed on the surface of phage particles, are well-known in the art. Additionally, bacterial surface expression vectors, yeast expression vectors and other eukaryotic expression vectors are well-known in the art.

Preferably the randomisation oligonucleotides used in each cycle of codon addition differ by having a different sequence, (N)$_b$. That is, in a first cycle the randomisation oligonucleotides have a first sequence (N)$_b$ with different randomisation codons. In a second, subsequent cycle the randomisation oligonucleotides have a second sequence (N)$_b$' attached to randomisation codons. This allows randomised oligonucleotides obtained after each randomised codon addition cycle to be amplified with a primer specific for the sequence (N)$_b$' or (N)$_b$.

Preferably, the expression vector is inserted into a suitable expression host cell, such as a bacterial cell (e.g. *E. coli*), yeast, etc. The host cell expresses the peptide encoded by the DNA library which is then used for further study.

Methods for producing a randomised peptide library comprising expression of the oligonucleotide library obtained by a method according to the invention are also provided.

The protein libraries obtainable by the methods of the invention are also provided.

The invention also provides a randomised oligonucleotide library comprising a plurality of oligonucleotides, each oligonucleotide having 3 or more contiguous randomised MAX codons which represent the optimum codon usage of a predetermined organism, and wherein the MAX codons are different between different members of the library.

Preferably, the randomised library comprises 1 or 2, most preferably 3, 4, 5, 6, 7, 8, 9 or 10 MAX codons. Kits for producing an oligonucleotide by a method according to the invention are also provided.

Preferably, the kit comprises a plurality of different randomisation oligonucleotides comprising:
(i) a coding strand, the coding strand comprising a randomisation codon; and
(ii) a substantially complementary non-coding strand,
wherein each double-stranded randomisation oligonucleotide comprises a nucleotide sequence coding for a restriction endonuclease recognition site capable of being recognised by a restriction endonuclease, the restriction endonuclease capable of cleaving the randomisation oligonucleotide upstream or downstream of the endonuclease recognition at a predetermined cleavage site to create a blunt ended cut.

Preferably, the recognition site is:

```
5'-GAGTCNNNNN^-3'     (SEQ. ID. No. 1)

3'-CTCAGNNNNN^-5'     (SEQ. ID. No. 2)
``` where—N=any nucleotide
^=the restriction endonuclease cleavage site.

The kit may additionally comprise a restriction enzyme capable of cleaving the randomisation oligonucleotide and the predetermined cleavage site. Preferably, the restriction endonuclease is selected from SchI and MlyI.

Preferably, the randomisation codons consist of MAX codons which represent the optimum codon usage of a predetermined organism of interest or a predetermined selection of said MAX codons.

The coding strand is preferably of the double-stranded randomisation oligonucleotide comprising a 5' end and a 3' end, the 3' end of the coding strand comprising a blocking group.

Preferably, the blocking group is selected from an amino group, a phosphate group, a glycerol moiety, a thiol group and a polyethylene glycol moiety.

Preferably, the non-coding strand comprises a 3' end and a 5' end, the 5' end of the non-coding strand extending one or more nucleotides beyond the 3' end of the complementary coding strand.

Preferably, the coding strand comprises the sequence:

```
(i)      5' XXX^(N)_aR'(N)_b-B 3'
or
(ii)     5'-(N)_bR(N)_a^XXX-3'
``` where:
XXX is the randomisation codon,
N is any nucleotide,
a is an integer of 0 to 10, preferably 5, b is an integer of 0 to 40, preferably 1 to 20, or preferably 1 to 10,
^ is the restriction endonuclease cleavage site,
R' is the reverse complement of the restriction endonuclease recognition site sequence,
R is the restriction endonuclease recognition site sequence,
B may or may not be present and when present may be selected from —OH, —NH$_2$, phosphate, a glyceryl moiety, a thiol and a polyethylene glycol moiety.

The kit may additionally comprise a predefined oligonucleotide comprising:
(i) a coding strand, the coding strand comprising a predefined codon coding for a predefined amino acid; and
(ii) a substantially complementary non-coding strand,
wherein the predefined oligonucleotide comprises a nucleotide sequence coding for a restriction endonuclease recognition site capable of being recognised by a restriction endonuclease, the restriction endonuclease capable of cleaving the predefined oligonucleotide upstream or downstream of the endonuclease recognition at a predetermined cleavage site to create a blunt ended cut.

The invention also provides host cells comprising a DNA library obtainable by a method according to the invention and/or utilising a kit according to the invention.

The kits may be used to produce peptide libraries for screening the effect of different sequences on, for example, the binding of ligands or for the effect on a biological activity of the peptide.

BRIEF DESCRIPTION OF THE DRAWINGS

The invention will now be described by way of example only with reference to the following figures.

EXAMPLE

Figure 1:
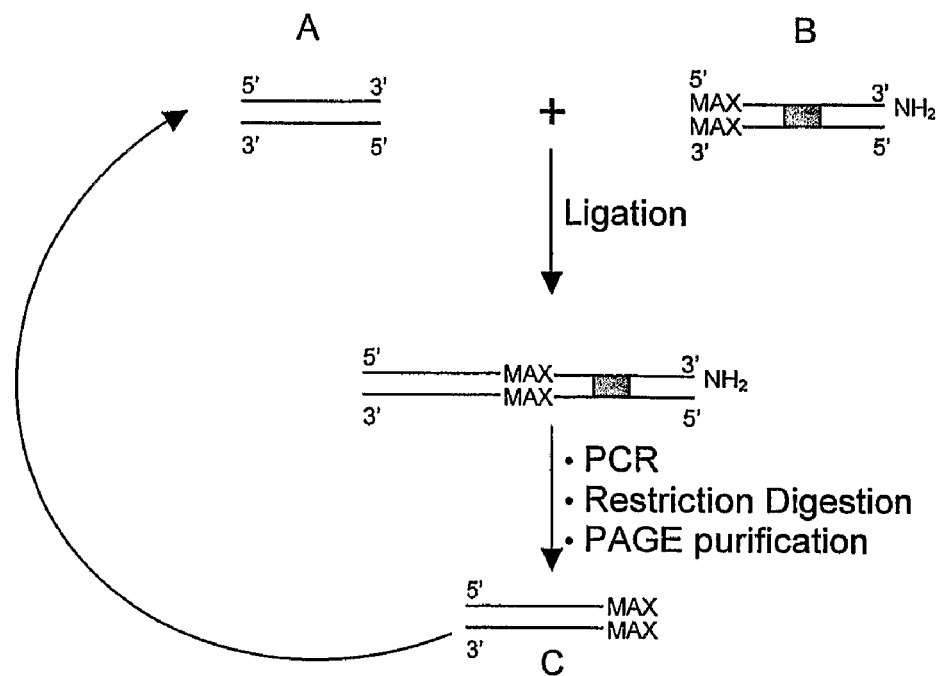
FIG. 1 shows schematically a method of producing DNA sequences containing MAX codons at predetermined positions according to the present invention.

FIG. 1 shows a schematic of the method used to generate the randomised DNA library containing MAX codons at the seven predetermined positions. MAX denotes a codon representing one of the 20 codons favoured in *E. coli*. NH$_2$ represents an amine group present at the 3' end of this oligonucleotide in order to minimise non-productive ligations. The grey box represents the MlyI restriction endonuclease site.

The principal steps involved in the production of the library are:
1. Hybridisation of the complementary pairs of oligonucleotides
2. Ligation of the starter A and randomisation oligonucleotides B
3. PCR amplification of the ligation product
4. Digestion with MlyI and purification of product by PAGE of product C
5. Repetition of the above process to achieve the desired number of contiguous randomised positions.
6. Cloning the DNA constructs into an appropriate vector
Hybridisation, ligation and cloning were performed as described below and the constructs transformed into *E. coli*

DH5a (genotype: F' 80dlacZ(lacZYA-argF)U169 deoR recA1 endA1 hsdR17(rK−, mK+)phoA supE44-thi-1 gyrA96 relA1/F' proAB+lacIqZM15 Tn10(tetr)) chemically competent cells, which were induced to take up DNA by heat shock. Clones were isolated and plasmid DNA recovered. The insert DNA was sequenced to establish the sequences present at the predetermined positions.

Any suitable host cell, and indeed alternative expression vectors, may be used instead of this strain of E. coli.

Materials and Methods

Starter DNA Synthesis

A fully complementary pair of starter DNA oligonucleotides were synthesised by MWG Biotech.

Randomisation Oligonucleotide Synthesis

Fully complementary pairs of randomisation oligonucleotides were synthesised by MWG Biotech. Randomisation oligonucleotides were designed to encode a single MAX codon at the 5' end and an amino group at the 3' end of the coding strand. The non-coding strand was not amino modified.

Phosphorylation

5' phosphorylation reactions of the coding strands of the randomisation oligonucleotides were set up in a final volume of 50 µl unless otherwise specified. The reactions consisted of 1× Ligase buffer (NEB—New England Biolabs), 10 units T4 PNK, 300 pmoles of DNA and water to a final volume of 50 µl. The reaction was incubated at 37° C. for 30 min and then the reaction stopped by raising the temperature to 65° C. for 20 min.

Hybridisation

Hybridisation reactions were set up using equal amounts of two oligonucleotides. The final volume of the reaction was 50 µl. This reaction was heated to 95° C. and held at that temperature for 2 min. The temperature was allowed to decrease by 1° C./min until 4° C. was to allow the complementary sequences to hybridise.

Ligations

Blunt end ligations were carried out between the starter and pool of 20 randomisation oligonucleotides. Ligations were set up using equal quantities of forward and reverse oligonucleotides (50 pmoles), 1× Ligase buffer (NEB), 10 units ligase (NEB) and water to a final volume of 20 il. The reaction was incubated at 26° C. overnight.

Polymerase Chain Reaction (PCR).

PCR reactions contained 1 unit of Pfu polymerase (Promega), 50 pmoles of each of the PCR primers, 1 µl of starter, 200 µM dNTP's, 1× Pfu buffer, and double distilled water to make the volume up to 100 µl. DNA was amplified using the following conditions: 94° C. for 30 seconds, 48° C. for 30 seconds, 72° C. for one minute for 35 cycles. The reactions were completed at 72° C. for 7 minutes and the samples stored at 4° C.

Phenol Chloroform Extraction of DNA.

A 0.1 volume of 3M sodium acetate (pH 5.2) was added to the DNA being purified reaction which was then mixed by vortexing. Subsequently one volume of phenol/chloroform/iso-amyl-alcohol (25:24:1) was added, and the sample vortexed and centrifuged for 2 min at 14000 rpm. The aqueous layer containing the DNA was removed carefully to a clean microfuge tube. One volume of chloroform was added and the resultant mixture vortexed and centrifuged for 2 min at 14000 rpm. The aqueous layer removed to a clean microfuge tube and 2 volumes of ice cold ethanol was added and the sample vortexed. The microfuge tube was placed at −20° C. overnight or at −70° C. for 1 hour and then allowed to thaw prior to centrifugation for 20 minutes at 14000 rpm. The supernatant was removed and the DNA pellet was washed with 200 µl of 70% ethanol. The supernatant was removed and the pellet was allowed to air dry prior to resuspension in distilled water. Samples were stored at −20° C. until required.

Restriction Digests of DNA.

Restriction digests were set up in 1× appropriate buffer (according to manufacturers' instructions) with 0.1 µg/µl of DNA, 10 units of restriction enzyme and made up to 20 il with double distilled water. The restriction digests were incubated at 37° C. or 55° C. for two hours as recommended by the manufacturer. The temperature was then raised to 65° C. for twenty minutes to denature the enzyme. Double digests were set up in the same way using the buffer most appropriate for the combination of enzymes.

Polyacrylamide Gel Electrophoresis.

Denaturing PAGE gels were prepared by dissolving 21 g urea, 12.5 ml of 40% acrylamide (19:1 acrylamide:bisacrylamide ratio), 5 ml TBE (10×) (0.9 MTris base, 0.9M Boric acid and 20 mM EDTA) and making to a final volume of 50 ml with water. This was stirred vigorously until the urea had dissolved, 600 µl of 10% ammonium persulphate was added and subsequently 80 µl of TEMED (N,N,N', N', tetraethylmethylethylene diamine). The electrophoresis apparatus was set up as per manufacturers' instruction and the gel poured and set. The samples were then loaded onto the gel and a voltage of 20V/cm applied for approximately 3 hours. The gel was then removed from the glass plates and placed into 1×TBE buffer with ethidium bromide at a concentration of 2 µg/ml. This was then placed on a shaker at 150 rpm and left for five minutes. The gel was then removed from the buffer and photographed under U.V light. When a non-denaturing PAGE was required, the gel was made in the same way but the urea was omitted.

Elution of DNA from PAGE.

The band of interest was excised from the gel and placed in a DNA/protein elution column. 1×TAE buffer (100 mM Tris base, 19 mM acetic acid and 0.2 mM EDTA) was added to the column and the lid applied tightly to prevent any leakage. The column was then immersed into a gel electrophoresis tank filled with 1×TAE buffer. A voltage of 15V/cm was applied for 20 min to allow the DNA to elute from the gel. After 20 min the current was reversed for 30 s to release the DNA from the membrane of the elution column into the buffer and the column removed from the rack. The buffer was carefully removed from the elution column and the DNA precipitated.

0.1 volume of 3M sodium acetate (pH 5.2) and 2 µl pellet paint were added to the extracted buffer. Two volumes of 100% ethanol were added and the sample was vortexed and incubated at room temperature for 1 min. The sample was then centrifuged at 14000 rpm for five min, the supernatant was removed, and the pellet was washed with 200 il of 70% ethanol. The supernatant was removed and the pellet was dried prior to resuspension in an appropriate amount of double distilled water.

Preparation of Chemically Competent E. coli (DH5α)

A single colony of E. coli (DH5α) was inoculated into 10 ml of SOB and incubated overnight at 37° C. in a shaker at 250 rpm. 8 ml of the overnight culture was transferred into 800 ml of LB. This was incubated at 37° C. in a shaker at 250 rpm until the culture was midway through the log phase (OD550 of ~0.45). The cells were then chilled on ice for 30 minutes and then pelleted by centrifugation at 4° C. The supernatant was then removed and the cells resuspended by gentle pipetting in 264 ml RF1 (100 mM RbCl, 50 mM $MnCl_2$, 30 mM potassium acetate, 10 mM $CaCl_2$, 15% glycerol, adjusted to pH 5.8 with 0.2M acetic acid). The resuspended cells were then incubated on ice for one hour. The cells were pelleted again and the supernatant removed. The cells were resuspended in 64 ml RF2 (10 mM MOPS (4-morpholinepropane-sulfonic acid), 10 mM RbCl, 75 mM CaCl$_2$, 15% glycerol, adjusted to pH 6.8 with NaOH) and incubated on ice for 15 minutes. They were dispensed in 200 µl aliquots in microfuge tubes which were then flash frozen in liquid nitrogen and stored at −70° C. until required.

Transformation

The competent *E. coli* (DH5α) were thawed on ice and 100 µl was added to the ligation mix (20 µl) swirled to mix and allowed to incubate on ice for 30 minutes. The cells were heat shocked at 37° C. for 45 seconds and returned to ice for a further two minutes. 100 µl of 2×LB was added to the cells and this allowed to incubate at 37° C. in a shaker at 250 rpm for 1 hour. 10 µl of IPTG and 50 µl of 2% X-gal was added to the cells prior to plating out on selective media.

Plasmid DNA Preparation.

Plasmid DNA was prepared for sequencing using Promega Wizard miniprep kit according to manufacturers' instructions.

DNA Sequencing

Automated DNA sequencing was performed by the Birmingham University Genomics laboratory on an ABI 3700 sequencer.

Results

Figure 2:
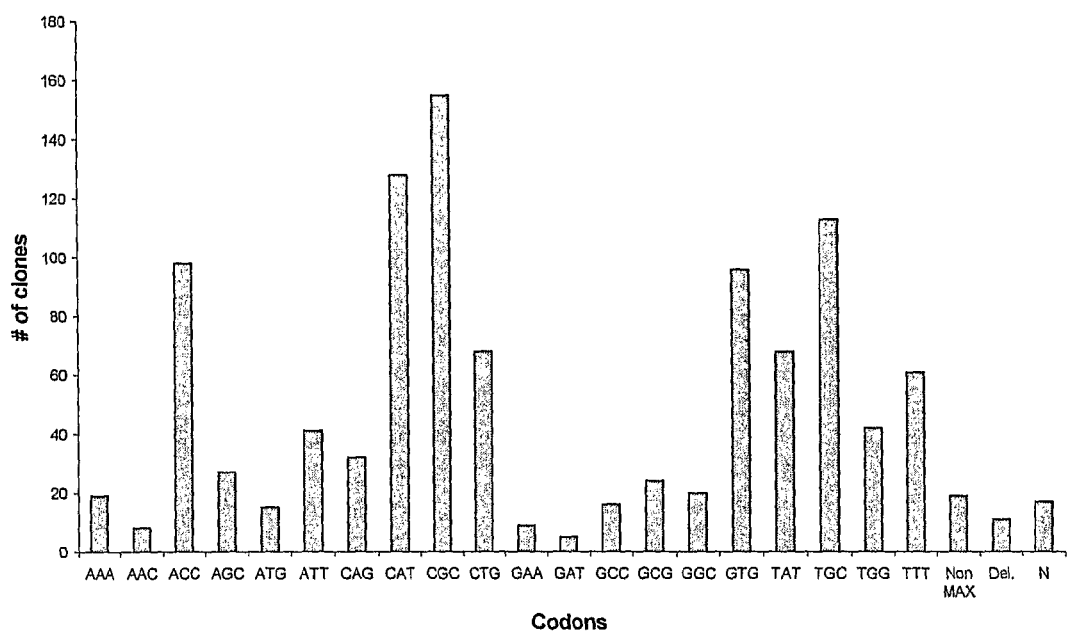
FIG. 2 shows the distribution of MAX codons and non-MAX codons at the predetermined positions within DNA sequences produced by the method of the present invention.

FIG. 2 shows the distribution of the different MAX codons obtained at the predetermined positions in the isolated clones. A total of 156 clones were sequenced, giving a total of 1092 MAX encoding positions. All 20 of the encoded sequences have been represented within the clones analysed. The column labelled 'non-MAX' refers to codons which have arisen but were not specified in the randomisation mix. The column labelled 'N' refers to those codons in which the sequence could not be determined due to a lack of clarity in the sequencing. The column labelled 'Del.' refers to those codons which were either not present or contained a deletion.

The technique has at this stage been used to produce at least 7 contiguous randomised codons.

In an alternative embodiment the MAX codon may be added at the opposite end of the starter oligonucleotide.

CONCLUSION

The technique provides a method of producing randomised oligonucleotides having randomised codons.

Alternative Method

Figure 3:
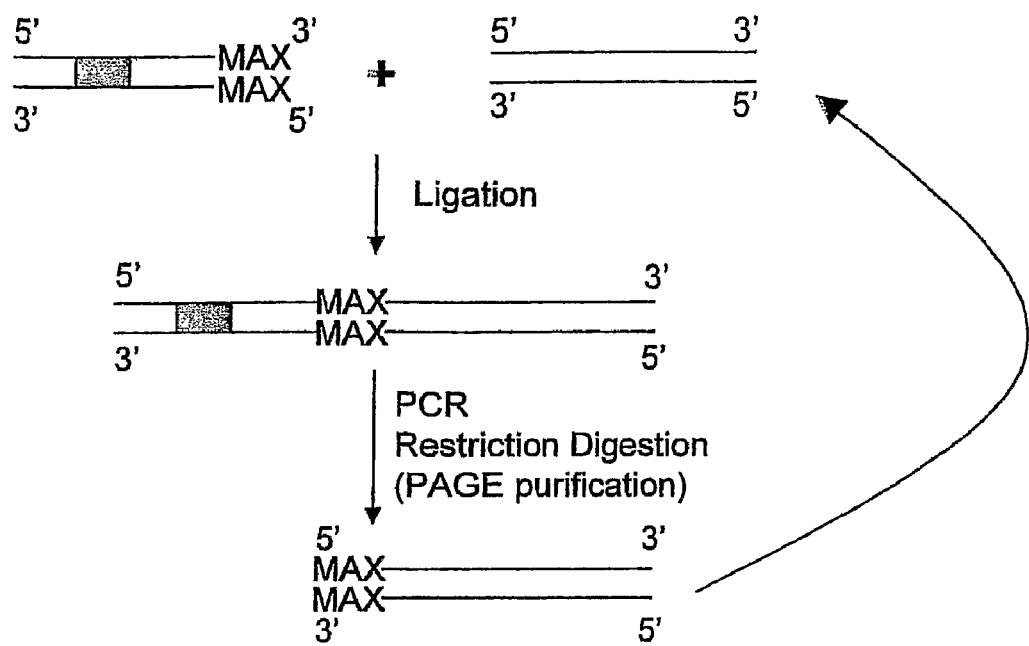
FIG. 3 shows a schematic diagram indicating an alternative method of the invention in which MAX codons are added at the opposite end of the starter oligonucleotide to that shown in FIG. 1.

FIG. 3 shows an alternative method of adding MAX codons. the MAX codons are added at the opposite end of the starter oligonucleotide to that shown in FIG. 1. The annotations are the same as for FIG. 1. This demonstrates that the technique may be used to introduce MAX codons at either end of a coding strand.

PAGE purification is bracketed as in this, and indeed in the system shown in FIG. 1, the need for PAGE may be reduced by using different randomisation oligonucleotides with different sequences up- or down-stream of the MAX codon in each round of MAX codon addition. This allows randomised double-stranded oligonucleotides obtained after each round of codon addition to be selectively amplified by PCR with a primer complementary to the different sequence.

The invention claimed is:

1. Method of producing an oligonucleotide library comprising a plurality of oligonucleotides, each oligonucleotide in the library having at least one predetermined position, a randomisation codon selected from a defined group of codons, the codons within said defined group coding for different amino acids, said method comprising the steps of:
   (a) Providing one or more double-stranded starter oligonucleotides, wherein the starter oligonucleotides comprise a blunt end;
   (b) Providing a plurality of different double stranded randomisation oligonucleotides comprising:
      (i) a coding strand, the coding strand comprising a randomisation codon; and
      (ii) a substantially complementary non-coding strand, wherein each double stranded randomisation oligonucleotide comprises a nucleotide sequence coding for a restriction endonuclease recognition site capable of being recognised by a restriction endonuclease, the restriction endonuclease capable of cleaving the randomisation oligonucleotide upstream or downstream of the endonuclease recognition site at a predetermined cleavage site to create a blunt ended cut;
   (c) Ligating each double-stranded starter oligonucleotide to a double-stranded randomisation oligonucleotide to form ligated oligonucleotides;
   (d) Amplifying the ligated oligonucleotides;
   (e) Digesting the ligated oligonucleotide with the restriction endonuclease to form a plurality of randomised double-stranded oligonucleotides, each of which comprise, at one end, a randomisation codon; and,
   (f) Using the randomised double-stranded oligonucleotides as starter oligonucleotides and repeating method steps (a) to (e) to produce a plurality of randomised double-stranded oligonucleotides, each comprising an additional randomisation codon;
      wherein step (f) is followed one or more times to produce an oligonucleotide library comprising a plurality of oligonucleotides, each oligonucleotide in the library having at least two contiguous randomised codons.

2. Method according to claim 1, wherein the endonuclease cleaves the randomisation oligonucleotide adjacent to the randomisation codon provided by the randomisation oligonucleotide.

3. Method according to claim 1, wherein the restriction endonuclease recognition site and cleavage site is:

```
5'-GAGTCNNNNN^-3'     (SEQ. ID. No. 1)

3'-CTCAGNNNNN^-5'     (SEQ. ID. No. 2)
``` where—N=any nucleotide
^=the restriction endonuclease cleavage site.

4. Method according to claim 3, wherein the restriction endonuclease is selected from SchI and MlyI.

5. Method according to claim 1, wherein the randomised group of codons are focused.

6. Method according to claim 1 wherein the randomised oligonucleotides used in each step (f) as defined in claim 1 comprise a different nucleotide sequence attached to the randomisation codon, compared with those used in a previous random codon addition cycles (steps (a) to (e)).

7. Method according to claim 1 additionally comprising ligating a completion oligonucleotide having a predefined sequence onto the randomised oligonucleotide after a predetermined number of randomisation codons have been added.

8. Method according to claim 1, wherein the randomisation codons consist of MAX codons which represent the optimum codon usage of a predetermined organism of interest or a predetermined selection of said MAX codons.

9. Method according to claim 1, the coding strand of the double-stranded randomisation oligonucleotide comprising a 5' end and a 3' end, the 3' end of the coding strand comprising a blocking group.

10. Method according to claim 9, wherein the blocking group is selected from an amino group, a phosphate group, a glyceryl moiety, a thiol group and a polyethylene glycol moiety.

11. Method according to claim 1, wherein the non-coding strand comprises a 3' end and a 5' end, the 5' end of the non-coding strand extending one or more nucleotides beyond the 3' end of the complementary coding strand.

12. Method according to claim 1, wherein the randomised double stranded starter oligonucleotide obtained in step (e) is purified.

13. Method according to claim 1 additionally comprising the steps of:
   (g) Providing a randomised double-stranded starter oligonucleotide produced by a method according to any preceding claim;
   (h) Providing a predefined oligonucleotide comprising:
      (i) a coding strand, the coding strand comprising a predefined codon coding for a predefined amino acid; and
      (ii) a substantially complementary non-coding strand,
   wherein the predefined oligonucleotide comprises a nucleotide sequence coding for a restriction endonuclease recognition site capable of being recognised by a restriction endonuclease, the restriction endonuclease capable of cleaving the predefined oligonucleotide upstream or downstream of the endonuclease recognition site at a predetermined cleavage site to create a blunt ended cut;
   (i) Ligating the randomised double-stranded starter oligonucleotide to the predefined oligonucleotide to form a ligated oligonucleotide;
   (j) Amplify the ligated oligonucleotide; and
   (k) Digest the ligated oligonucleotide with the restriction endonuclease to form a randomised oligonucleotide comprising at one end the predefined codon.

14. Method according to claim 13, additionally comprising the steps of using the randomised oligonucleotide comprising the predefined codon as a starter oligonucleotide and repeating method steps (a) to (e), and optionally step (f) as defined in claim 1 to add one or more additional random codons to the oligonucleotides.

15. Method according to claim 1, additionally comprising the step of inserting an oligonucleotide obtained from a method carried out as defined in any preceding claim into an expression vector.

16. A method according to claim 1, wherein the expression vector is inserted into an expression host cell.

* * * * *

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial
<220> FEATURE:
<223> OTHER INFORMATION: restriction endonuclease recognition site
<220> FEATURE:
<221> NAME/KEY: misc_feature
<222> LOCATION: (6)..(10)
<223> OTHER INFORMATION: n is a, c, g, t or u

<400> SEQUENCE: 1 gagtcnnnnn                                                          10

<210> SEQ ID NO 2
<211> LENGTH: 10
<212> TYPE: DNA
<213> ORGANISM: Artificial
<220> FEATURE:
<223> OTHER INFORMATION: restriction endonuclease recognition site
<220> FEATURE:
<221> NAME/KEY: misc_feature
<222> LOCATION: (1)..(5)
<223> OTHER INFORMATION: n is a, c, g, t or u

<400> SEQUENCE: 2 nnnnngactc                                                          10
```